United States Patent [19]

Wachter et al.

[11] Patent Number: 5,962,663
[45] Date of Patent: *Oct. 5, 1999

[54] CATIONIC BIOPOLYMERS

[75] Inventors: Rolf Wachter, Duesseldorf, Germany; Holger Tesmann, Juechen, Norway; Ronald Svenning, Krokelvdalen, Norway; Ragnar Olsen, Tromso, Norway; Even Stenberg, Kvaloysletta, Norway

[73] Assignees: Henkel Kommanditgesellschaft auf Aktien, Duesseldorf, Germany; Norwegian Institute of Fisheries and Aquaculture Ltd., Tromso, Norway

[*] Notice: This patent issued on a continued prosecution application filed under 37 CFR 1.53(d), and is subject to the twenty year patent term provisions of 35 U.S.C. 154(a)(2).

[21] Appl. No.: 08/696,983
[22] PCT Filed: Nov. 23, 1995
[86] PCT No.: PCT/EP95/04624
  § 371 Date: Mar. 10, 1997
  § 102(e) Date: Mar. 10, 1997
[87] PCT Pub. No.: WO96/16991
  PCT Pub. Date: Jun. 6, 1996

[30] Foreign Application Priority Data

Dec. 2, 1994 [DE] Germany ............ P 44 42 987

[51] Int. Cl.$^6$ .................................................. C08B 37/08
[52] U.S. Cl. .............. 536/20; 536/124; 424/70.13; 424/78.02; 424/400; 514/55
[58] Field of Search ............... 536/20, 124; 424/70.13, 424/78.02, 400; 514/55

[56] References Cited

U.S. PATENT DOCUMENTS

| | | | |
|---|---|---|---|
| 2,040,879 | 5/1936 | Rigby | 536/20 |
| 3,547,828 | 12/1970 | Mansfield | 252/351 |
| 3,707,535 | 12/1972 | Lew | 536/18.6 |
| 3,772,269 | 11/1973 | Lew | 536/4.1 |
| 3,839,318 | 10/1974 | Mansfield | 536/18.6 |
| 4,172,887 | 10/1979 | Vanlerberghe et al. | 424/70 |
| 4,349,669 | 9/1982 | Klahr et al. | 536/127 |
| 4,923,976 | 5/1990 | Arnaudis | 536/18.6 |
| 5,442,048 | 8/1995 | Meister et al. | 536/20 |

FOREIGN PATENT DOCUMENTS

| | | |
|---|---|---|
| 2 101 079 | 8/1994 | Canada . |
| 077 167 | 4/1983 | European Pat. Off. . |
| 382 150 | 8/1990 | European Pat. Off. . |
| 2 252 840 | 8/1975 | France . |
| 2 701 029 | 8/1994 | France . |
| 2 701 266 | 8/1994 | France . |
| 11 65 574 | 3/1964 | Germany . |
| 19 43 689 | 3/1970 | Germany . |
| 20 36 472 | 2/1971 | Germany . |
| 20 24 051 | 12/1971 | Germany . |
| 30 01 064 | 7/1981 | Germany . |
| 1 333 475 | 10/1973 | United Kingdom . |
| 91/05808 | 5/1991 | WIPO . |

OTHER PUBLICATIONS

Sandford et al., Biomedical Applications of High–Purity Chitosan, In "Water Soluble Polymers: Synthesis, Solution Properties, and Applications", ACS Symposium Series 467, Shalaby et al., American Chemical Society, Washington, DC, 1991, 430–445. Month not available.
Ullmann's Encyclopedia of Industrial Chemistry, 5th Ed., vol. A6, Weinheim, Verlag Chemie, 1986, pp. 231–332.
Gesslein et al., Happi 27, (Oct. 1990) p. 57.
Skaugrud, Drug Cosm. Ind. 148 (May 1991), p. 24.
Onsøyen et al. Seifen–Öle–Fette–Wachse, 117 (1991) p. 633.
Sannan et al. Makromolekulare Chemie, 177 (1976), pp. 3589–3600.
Brine; Chitin: Accomplishments and Perspectives, In *Chitin, Chitosan and Related Enzymes*, Academic Press, 1984, pp. XVII to XXIV and pp. 239 to 255, John P. Zikakis, editor.
Surfactants in Consumer Products, Springer Verlag, Berlin, 1987, pp. 54 to 124, J. Falbe, editor.
Katalysatoren, Tenside und Mineraöladditive (Catalysts, Surfactants and Mineral Oil Additives), Thieme Verlag, Stuttgart, 1978, pp. 123–217, J. Falbe et al., editors. In German.
Kosmetische Färbemittel of the Farbstoffkommission der Deutschen Forschungsgemeinschaft, published by Verlag Chemie, Weinheim, 1984, pp. 81–106.
Whistler, Roy L., editor *Methods In Carbohydrate Chemistry*, Academic Press, vol. V, 1965, pp. 103–106, 403–406.

*Primary Examiner*—Kathleen K. Fonda
*Attorney, Agent, or Firm*—Wayne C. Jaeschke; John E. Drach; Steven J. Trzaska

[57] ABSTRACT

The invention relates to new cationic biopolymers with an average molecular weight of 800,000 to 1,200,000 Dalton, a Brookfield viscosity (1% by weight in glycolic acid) below 5,000 mPas, a degree of deacetylation of 80 to 88% and an ash content of less than 0.3% by weight which are obtained by repeatedly subjecting crustacean shells to alternate acidic and alkaline degradation under defined conditions. Compared with known cationic biopolymers of the chitosan type, the new biopolymers form clear solutions and, at the same time, show excellent film-forming properties, despite their high molecular weight.

8 Claims, No Drawings

CATIONIC BIOPOLYMERS

This is the U.S. National Stage entry under 35 U.S.C. 371 of PCT/EP95/04624, filed Nov. 23, 1995.

BACKGROUND OF THE INVENTION

1. Field of the Invention

This invention relates to cationic biopolymers obtained by demineralization, deproteinization, decalcification and deacetylation of fresh crustacean shells, to a process for their production and to their use for the production of cosmetic and pharmaceutical formulations.

2. Statement of Related Art

Chitosans are biopolymers which belong to the group of hydrocolloids. Chemically, they are partly deacetylated chitins varying in molecular weight which contain the idealized monomer unit (I).

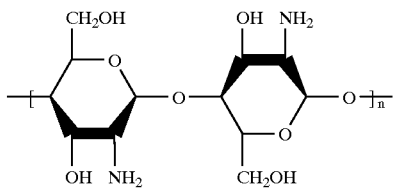

In contrast to most hydrocolloids, which are negatively charged at biological pH values, chitosans are cationic biopolymers under these conditions. The positively charged chitosans are capable of interacting with oppositely charged surfaces and, accordingly, are used in cosmetic hair-care and body-care formulations and pharmaceutical formulations (cf. Ullmann's Encyclopedia of Industrial Chemistry, 5th Ed., Vol. A6, Weinheim, Verlag Chemie, 1986, pp. 231–332). Reviews on this subject have been published, for example, by B. Gesslein et al. in HAPPI 27, 57 (1990), by O. Skaugrud in Drug Cosm. Ind. 148, 24 (1991) and by E. Onsoyen et al. in Seifen-Öle-Fette-Wachse 117, 633 (1991).

Chitosans are produced from chitin, preferably from the shell remains of crustaceans which are available in large quantities as inexpensive raw materials. Normally, the chitin is first deproteinized by addition of bases, demineralized by addition of mineral acids and, finally, deacetylated by addition of strong bases in a process described for the first time by Hackmann et al., the molecular weights being spread over a broad range.

A process for the production of a chitin degradation product is known from Makromol. Chem. 177, 3589 (1976). In this process, the Hackmann degradation is modified to the extent that the crab shells are first treated with hydrochloric acid at room temperature, then deacetylated with caustic soda solution over a period of 42 h at 100° C., subsequently treated with more hydrochloric acid at room temperature and, finally, briefly aftertreated with sodium hydroxide solution, again at room temperature. In this process, the deacetylation takes place in the second step. By contrast, the concluding treatment with sodium hydroxide solution is merely carried out to "fine tune" the degree of deacetylation and, accordingly, takes place at room temperature. Although this leads to low-ash products with a high degree of deacetylation and good solubility in organic acids, the molecular weight is very low and the film-forming properties are unsatisfactory.

The book "Chitin, Chitosan and Related Enzymes" (Ed. John P. Zikakis), New York, Academic Press, 1984, pp. XVII to XXIV and pp. 239 to 255, also relates inter alia to degradation products of chitin which, although having a low ash content according to Table 1 on p. 248 ("Chitin D"), have an extremely low degree of deacetylation of only 17.1%. Unfortunately, products such as these are completely insoluble in organic acids.

French patent application FR-A 27 01 266 also describes degradation products which are obtained by first treating chitin with hydrochloric acid and then deacetylating it as far as possible with sodium hydroxide solution. The products obtained typically have a degree of deacetylation of 92% and are distinguished by a very low calcium carbonate content, are readily soluble in organic acids and give low-viscosity products. However, a major disadvantage once again is that the molecular weight is very low on account of the drastic degradation conditions and the film-forming properties of the products are again unsatisfactory.

Finally, WO 91/05808 (Firextra Oy) and EP-B1 0 382 150 (Hoechst) describe processes for the production of optionally microcrystalline chitosan.

To sum up, it may be said that known cationic biopolymers can be divided into two groups: the first group of products includes those which have a high degree of deacetylation, are soluble in organic acids and form low-viscosity solutions, but do not have satisfactory film-forming properties. The second group includes products which have a low degree of deacetylation, a relatively high molecular weight and good film-forming properties, but are poorly soluble in organic acids and, accordingly, are difficult to make up.

In addition, known products have a number of other disadvantages. As a result of the drastic degradation, they are generally heavily discolored, have an unacceptable odor and lack stability in storage, i.e. viscosity does not remain constant, but decreases, in the event of prolonged storage. Moreover, preservatives unfortunately have to be added because the products are susceptible to contamination by microorganisms.

Accordingly, the complex problem addressed by the present invention was to provide new cationic biopolymers which would be free from the disadvantages mentioned above, i.e. which would have a high molecular weight but would still be readily soluble in organic acids, forming low-viscosity solutions therein, and which would show excellent film-forming properties despite a high degree of deacetylation.

DESCRIPTION OF THE INVENTION

The invention relates to new cationic biopolymers which have an average molecular weight of 800,000 to 1,200,000 and preferably 900,000 to 1,000,000 Dalton, a Brookfield viscosity (1% by weight in glycolic acid) below 5,000 mPas, a degree of deacetylation of 80 to 88 and preferably 82 to 85% and an ash content of less than 0.3% by weight and preferably less than 0.1% by weight and which are obtained by (a) treating fresh crustacean shells with dilute aqueous mineral acid, (b) treating the resulting demineralized first intermediate product with aqueous alkali metal hydroxide solution, (c) treating the resulting lightly deproteinized second intermediate product with more dilute aqueous mineral acid, (d) optionally drying the resulting decalcified third intermediate product to a residual water content of 5 to 25% by weight and (e) finally deacetylating the optionally dried product with concentrated aqueous alkali metal hydroxide, steps (a) and (c) being carried out at a temperature of 15 to 25° C. and at a pH value of 0.3 to 0.7 and steps (b) and (e) being carried out at a temperature of 70 to 110° C. and at a pH value of 12 to 14.

It has surprisingly been found that cationic biopolymers essentially obtained by deacetylation of chitin from marine animals solve the problem stated above when the basically known process of alternate acidic and alkaline degradation is carried out in the described manner with strict adherence to the sequence of individual steps and the pH and temperature ranges. New cationic biopolymers are obtained which, despite their high molecular weight, are readily and completely soluble in organic acids and, at the same time, have superior film-forming properties. In addition, the products are light-colored, stable in storage and protected against contamination without the addition of preservatives. The substances differ so significantly in their property profile from known biopolymers that they may be regarded as new substances in their own right.

The present invention also relates to a process for the production of cationic biopolymers having an average molecular weight of 800,000 to 1,200,000 and preferably 900,000 to 1,000,000 Dalton, a Brookfield viscosity (1% by weight in glycolic acid) below 5,000 mPas, a degree of deacetylation of 80 to 88 and preferably 82 to 85% and an ash content of less than 0.3% by weight and preferably less than 0.1% by weight, comprising the steps of (a) treating fresh crustacean shells with dilute aqueous mineral acid, (b) treating the resulting demineralized first intermediate product with aqueous alkali metal hydroxide solution, (c) treating the resulting lightly deproteinized second intermediate product with dilute aqueous mineral acid, (d) optionally drying the resulting decalcified third intermediate product to a residual water content of 5 to 25% by weight and (e) finally deacetylating the optionally dried product with concentrated aqueous alkali metal hydroxide, steps (a) and (c) being carried out at a temperature of 15 to 25° C. and at a pH value of 0.3 to 0.7 and steps (b) and (e) being carried out at a temperature of 70 to 110° C. and at a pH value of 12 to 14.

Starting Materials

Suitable starting materials are shells of crustaceans, preferably crayfish, crab, shrimp or krill shells. In view of contamination by endotoxins and the antimicrobial stabilization of the end products, it has proved to be of advantage to use freshly caught raw materials. In practical terms, this can mean, for example, that the shells of freshly caught crabs are removed on board ship and then deep-frozen pending further processing. It is of course also possible to freeze the entire catch and to further process it on land.

Demineralization

Demineralization is the particularly important first step of the process according to the invention because endotoxins are also removed in this way, deproteinization is made considerably easier and, finally, the foundations for the production of particularly low-ash biopolymers are laid. Demineralization is carried out by treating the shells with aqueous mineral acids, preferably dilute hydrochloric acid, at a temperature of 15 to 25° C. and preferably of the order of 20° C. and at a pH value of 0.3 to 0.7 and preferably of the order of 0.5.

Deproteinization

Deproteinization is carried out by treating the demineralized intermediate products with aqueous alkali metal hydroxide solutions, preferably dilute 5 to 25% by weight sodium hydroxide solution. This step is preferably carried out a temperature of 50 to 110° C. and, more particularly, 90 to 108° C. and at a pH value of 12 to 14.

Decalcification

Decalcification is carried out in the same way as the demineralization step. In this case, too, the now deproteinized intermediate product is treated with aqueous mineral acids at a temperature of 15 to 25° C. and preferably at a temperature of around 20° C. and at a pH value of 0.3 to 0.7 and preferably of the order of 0.5. It has proved to be of advantage to dry the decalcified intermediate product to a residual water content of 5 to 25% by weight, based on the non-dewatered product, before the subsequent deacetylation step.

Deacetylation

Deacetylation is carried out using concentrated bases, for example concentrated 50 to 70% by weight sodium or potassium hydroxide, again at a temperature of 70 to 110° C., and, more particularly, 90 to 108° C. and at a pH value of 12 to 14. The degradation process is preferably carried out in boiling sodium hydroxide solution and is continued until a biopolymer containing 0.1 to 0.25 and preferably 0.16 to 0.2 mole of acetamide per mole of monomer unit—corresponding to a degree of deacetylation of 80 to 88 and preferably 82 to 85%—is obtained. The degree of deacetylation may largely be established through the reaction time which is normally between 1 and 10 h and preferably between 2 and 5 h. It has also proved to be of advantage to wash the intermediate products until neutral before each new process step.

COMMERCIAL APPLICATIONS

The new cationic biopolymers are distinguished by the fact that, in dilute aqueous solutions, they form gels of extremely high viscosity, build up films and are largely stabilized against microbial contamination. Accordingly, the present invention also relates to the use of the new biopolymers for the production of cosmetic and/or pharmaceutical formulations such as, for example, hair-care or skin-care preparations, hair-repair preparations and wound-healing preparations, in which they may be present in quantities of 0.01 to 5% by weight and preferably 0.1 to 1.5% by weight, based on the particular preparation.

Auxiliaries and Additives

The skin-care and hair-care formulations containing the new cationic biopolymers may contain surfactants compatible therewith.

Typical examples of anionic surfactants are alkylbenzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, protein fatty acid condensates (more particularly wheat-based vegetable products) and alkyl(ether) phosphates. If the anionic surfactants contain polyglycol ether chains, they may have a conventional homolog distribution although they preferably have a narrow-range homolog distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides, fatty acid N-alkyl glucamides, protein hydrolyzates (more especially wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Typical examples of cationic surfactants are quaternary ammonium compounds and esterquats, more particularly quaternized fatty acid trialkanolamine ester salts.

Typical examples of amphoteric or zwitterionic surfactants are alkylbetaines, alkylamidobetaines, aminopropionates, aminoglycinates, imidazolinium betaines and sulfobetaines.

The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217. Nonionic, cationic, amphoteric and/or zwitterionic surfactants, such as preferably alkyl and/or alkenyl oligoglucosides, fatty acid N-alkyl glucamides, alkylamidobetaines, protein hydrolyzates, quaternary ammonium compounds and esterquats, are particularly preferred. The surfactants may be present in the formulations in quantities of 0.5 to 15% by weight, based on the formulation.

Skin-care formulations, such as creams, lotions and the like and also perfumes, after-shaves, tonics, sprays and decorative cosmetic products, generally contain oil components, emulsifiers, fats and waxes, stabilizers, superfatting agents, thickeners, biogenic agents, film formers, preservatives, dyes and fragrances in addition to the surfactants already mentioned.

Hair-care formulations, such as for example hair shampoos, hair lotions, hair sprays, foam baths and the like, may contain emulsifiers, superfatting agents, thickeners, biogenic agents, film formers, cationic polymers, silicones, preservatives, dyes and fragrances as further auxiliaries and additives in addition to surfactants compatible with the biopolymers.

Suitable oils are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer diol) and/or Guerbet alcohols, triglycerides based on $C_{6-10}$ fatty acids, vegetable oils, branched primary alcohols, substituted cyclohexanes, Guerbet carbonates, dialkyl ethers and/or aliphatic or naphthenic hydrocarbons.

Nonionic, ampholytic and/or zwitterionic surface-active compounds distinguished by a lipophilic, preferably linear, alkyl or alkenyl group and at least one hydrophilic group may be used as emulsifiers or co-emulsifiers. The hydrophilic group may be both an ionic group and a nonionic group.

Nonionic emulsifiers contain, for example, a polyol group, a polyalkylene glycol ether group or a combination of a polyol and a polyglycol ether group as the hydrophilic group. Preferred formulations are those containing nonionic surfactants from at least one of the following groups as o/w emulsifiers:

(a1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group;

(a2) $C_{12/18}$ fatty acid monoesters and diesters of adducts of 1 to 30 moles of ethylene oxide with glycerol;

(a3) glycerol monoesters and diesters and sorbitan monoesters and diesters of saturated and unsaturated fatty acids containing 6 to 22 carbon atoms and ethylene oxide adducts thereof;

(a4) Alkyl mono- and oligoglycosides containing 8 to 22 carbon atoms in the alkyl group and ethoxylated analogs thereof and (a5) adducts of 15 to 60 moles of ethylene oxide with castor oil and/or hydrogenated castor oil;

(a6) polyol esters and, in particular, polyglycerol esters such as, for example, polyglycerol polyricinoleate or polyglycerol poly-12-hydroxystearate.

Mixtures of compounds from several of these classes are also suitable.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051. $C_{8/18}$ alkyl monoglycosides and oligoglycosides, their production and their use as surfactants are known, for example, from U.S. Pat No. 3,839,318, U.S. Pat. No. 3,707, 535, U.S. Pat. No. 3,547,828, DE-OS 19 43 689, DE-OS 20 36 472 and DE-A1 30 01 064 and from EP-A 0 077 167. They are produced in particular by reaction of glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical-grade products is based.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Suitable w/o emulsifiers are:

(b1) adducts of 2 to 15 moles of ethylene oxide with castor oil and/or hydrogenated castor oil;

(b2) partial esters based on linear, branched, unsaturated or saturated $C_{12/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose);

(b3) trialkyl phosphates;

(b4) wool wax alcohols;

(b5) polysiloxane/polyalkyl polyether copolymers and corresponding derivatives;

(b6) mixed esters of pentaerythritol, fatty acids, citric acid and fatty alcohol according to DE-PS 11 65 574 and (b7) polyalkylene glycols.

Suitable cationic polymers are, for example, cationic cellulose derivatives, cationic starch, copolymers of diallyl ammonium salts and acrylamides, quaternized vinyl pyrrolidone/vinyl imidazole polymers such as, for example, Luviquat® (BASF AG, Ludwigshafen, FRG), condensation products of polyglycols and amines, quaternized collagen polypeptides such as, for example, Lauryldimonium Hydroxypropyl Hydrolyzed Collagen (Lamequat®L, Grünau GmbH), polyethyleneimine, cationic silicone polymers such as, for example, Amidomethicone or Dow Corning, Dow Corning Co., USA, copolymers of adipic acid and dimethylaminohydroxypropyl diethylenetriamine (Cartaretine®, Sandoz AG, CH), polyaminopolyamides as described, for example, in FR-A 2 252 840 and crosslinked water-soluble polymers thereof, cationic chitin derivatives such as, for example, quaternized chitosan, optionally in microcrystalline distribution, cationic guar gum such as, for example, Jaguar® CBS, Jaguar® C-17, Jaguar® C-16 of Celanese, USA, quaternized ammonium salt polymers such as, for example, Mirapol® A-15, Mirapol® AD-1, Mirapol® AZ-1 of Miranol, USA.

Suitable silicone compounds are, for example, dimethyl polysiloxanes, methylphenyl polysiloxanes, cyclic silicones and amino-, fatty acid-, alcohol-, polyether-, epoxy-, fluorine- and/or alkyl-modified silicone compounds. In the context of the invention, biogenic agents are, for example, plant extracts and vitamin complexes. Typical film formers are, for example, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Superfatting agents may be selected from such substances as, for example, polyethoxylated lanolin derivatives, lecithin derivatives, polyol fatty acid esters, monoglycerides and fatty acid alkanolamides, the fatty acid alkanolamides also serving as foam stabilizers. Typical examples of fats are glycerides while suitable waxes are inter alia beeswax, paraffin wax or microwaxes, optionally in combination with hydrophilic waxes, for example cetostearyl alcohol. Metal salts of fatty acids such as, for example, magnesium, aluminium and/or zinc stearate may be used as stabilizers. In the context of the invention, biogenic agents are, for example, plant extracts and vitamin complexes. Suitable preservatives are, for example, phenoxyethanol, formaldehyde solution, parabens, pentanediol or sorbic acid. Suitable pearlescers are, for example, glycol distearic acid esters, such as ethylene glycol distearate, and also fatty acid monoglycol esters. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

The total percentage content of auxiliaries and additives may be 1 to 50% by weight and is preferably 5 to 40% by weight, based on the formulation. The formulations may be produced in known manner, i.e. for example by hot emulsification, cold emulsification, hot-hot/cold emulsification and PIT emulsification. These are purely mechanical processes which do not involve any chemical reactions.

The following Examples are intended to illustrate the invention without limiting it in any way.

EXAMPLES

I. Production Examples

Example 1

1,000 g of freshly removed crab shells (ash content 31.8% by weight, based on dry weight) were dried and treated for 12 h at 18° C. with 3,000 ml of dilute, 1-molar hydrochloric acid at a pH value of 0.5. The demineralized product was then washed until neutral; the ash content, based on dry weight, was 0.79% by weight. 15% by weight sodium hydroxide solution was added to the demineralized product in a ratio by weight of 1:3, followed by stirring for 2 h at 70° C. The deproteinized product was then kept for 18 h at 30° C. The resulting material was again washed until neutral; the ash content, based on dry weight, was 0.6% by weight. 1-Molar hydrochloric acid was added to the deproteinized product in a ratio by weight of 1:3. The mixture was gently stirred for about 1.5 h at 18° C. and then washed until neutral. The decalcified, light pink-colored product had an ash content, based on dry weight, of 0.08% by weight and was largely freed from adhering water by pressing before subsequent processing. The decalcified product was dissolved in boiling sodium hydroxide (70% by weight) in a ratio by weight of 1:4 and kept therein for 4 h at 108° C. The resulting biopolymer was washed with water until neutral, freeze-dried and ground. A pale pink-colored powder was obtained. The results are set out in Table 1. The molecular weights were determined by HPLC and the degrees of deacetylation by $^1$H NMR spectroscopy.

Example 2

The procedure was as in Example 1, except that the deacetylation was carried out over a period of 2 h. The results are set out in Table 1.

Example 3

The procedure was as in Example 1, but without the intermediate drying. The results are set out in Table 1.

Comparison Example C1

3 Liters of 1N hydrochloric acid were added to 1,000 g of fresh crustacean shells over a period of 24 h at room temperature. After washing until neutral, 5% by weight of 2N sodium hydroxide were added and the whole was stirred for 3 h at 90° C., followed again by washing until neutral. The Comparison Example corresponds to Example 1 of FR-A 27 01 266. The results are set out in Table 1.

Comparison Example C2

3 Liters of 2N hydrochloric acid were added to 1,000 g of fresh crustacean shells over a period of 5 h at room temperature. After washing until neutral, 5 liters of 2N sodium hydroxide were added and the whole was stirred for 36 h at 100° C., followed by washing until neutral, stirring for 2 h at room temperature with 5 liters of 2N hydrochloric acid, washing until neutral, treatment with 1 liter of 1N sodium hydroxide for 1 h at room temperature and, finally, washing until neutral. The Comparison Example corresponds to the modified Hackmann degradation as described in Makromol. Chem. 177, 3589 (1976). The results are set out in Table 1.

Comparison Examples C3 and C4

In these Examples, cationic biopolymers from Ajinomoto of Japan, i.e. commercially available products, were investigated.

TABLE 1

Solubility[1], Viscosity[2] and Flexural Strength[3]

| Ex. | Mol. Weight Dalton | Degree of Deacetylation %-rel. | Solubility | Viscosity mPas | Flexural Strength %-rel. |
|---|---|---|---|---|---|
| 1 | 1,000,000 | 84 | + | 2,500 | 260 |
| 2 | 1,000,000 | 83 | + | 2,500 | 250 |
| 3 | 900,000 | 85 | + | 2,500 | 260 |
| C1 | 270,000 | 92 | + | 2,500 | 50 |
| C2 | 260,000 | 95 | + | 1,800 | 40 |
| C3 | 1,000,000 | 55 | − | Not measurable | 120 |
| C4 | 500,000 | 83 | − | Not measurable | 110 |

[1] To determine solubility, the products were freeze-dried and dissolved in glycolic acid to form a 1% by weight solution (pH value 5.4). The evaluation "+" means "spontaneously and completely dissolved" whereas the evaluation "−" means "portions still undissolved after stirring for 2h".*
[2] The viscosity of the 1% by weight solutions was determined by the Brookfield method in an RVF viscosimeter (spindle 5, 10 r.p.m.).
[3] To determine flexural strength, a hair tress was treated with a 1% by weight solution of the test polymer, held between two points and subjected in the middle to a weight of 150 g of water (standard = 100%). The weight was increased until the hair tress sagged and the result was expressed relative to the standard.

The Examples and Comparison Examples show that only the products according to the invention, which have a selected molecular weight and an advantageous degree of deacetylation, simultaneously fulfil the viscosity, solubility and flexural strength requirements.

II. Formulation Examples

TABLE 2

Skin Care Formulations*

| Example | Ingredient | CTFA Nomenclature | % Content |
|---|---|---|---|
| Soft Cream | Emulgade ® SE | Glycerin Stearate (and) Ceteareth-20 (and) Ceteareth-12 | 5.0 |
| | Cetiol ® V | Decyl Oleate | 3.0 |
| | Cetiol ® SN | Cetearyl Isononanoate | 3.0 |
| | Glycerol 86% | | 3.0 |
| | Cationic biopolymer | | 40.0 |
| Moisturizing Emulsion | Emulgade ® SE | Glycerin Stearate (and) Ceteareth-20 (and) Ceteareth-12 | 5.0 |
| | Cetiol ® V | Decyl Oleate | 3.0 |
| | Cetiol ® SN | Cetearyl Isononanoate | 3.0 |
| | Glycerol 86% | | 3.0 |
| | Cationic biopolymer | | 60.0 |
| Anti-Wrinkle Cream | Lameform ® TGI | Polyglyceryl-3 Diisostearate | 4.0 |
| | Monomuls ® 90-O 18 | Glyceryl Oleate | 2.0 |
| | Beeswax | | 7.0 |
| | Cetiol ® OE | Dicapryl Ether | 5.0 |
| | Eutanol ® G | Octyidodecanol | 10.0 |
| | Cetiol ® LC | Coco Capryl Caprate | 5.0 |
| | Glycerol 86% | | 5.0 |
| | Magnesium sulfate | | 1.0 |
| | Cationic biopolymer | | 5.0 |
| Restoration Care | Lameform ® TGI | Polyglyceryl-3 Diisostearate | 4.0 |
| | Monomuls ® 90-O 18 | Glyceryl Oleate | 2.0 |
| | Beeswax | | 7.0 |
| | Cetiol ® OE | Dicapryl Ether | 5.0 |
| | Eutanol ® G | Octyldodecanol | 10.0 |
| | Cetiol ® LC | Coco Capryl Caprate | 5.0 |
| | Glycerol 86% | | 5.0 |
| | Magnesium sulfate | | 1.0 |
| | Cationic biopolymer | | 10.0 |
| Intensive Care | Cetiol ® OE | Dicapryl Ether | 5.0 |
| | Cetiol ® LC | Coco Capryl Caprate | 5.0 |
| | Emulgade ® SE | Glycerin Stearate (and) Ceteareth-20 (and) Ceteareth-12 | 4.5 |
| | Eumulgin ® B2 | Ceteareth-20 | 1.0 |
| | Cationic biopolymer | | 5.0 |
| Regeneration Emulsion | Cetiol ® OE | Dicapryl Ether | 5.0 |
| | Cetiol ® LC | Coco Capryl Caprate | 5.0 |
| | Emulgade ® SE | Glycerin Stearate (and) Ceteareth-20 (and) Ceteareth-12 | 4.5 |
| | Eumulgin ® B2 | Ceteareth-20 | 1.0 |
| | Cationic biopolymer | | 10.0 |
| Intensive Skin Care Fluid | Emulgade ® PL 1618 | Hexadecyl Polyglucose (and) Hexadecyl Alcohol | 7.5 |
| | Cetiol ® J 600 | Oleyl Erucate | 4.0 |
| | Myritol ® 318 | Capryliclcapric Triglyceride | 4.0 |
| | Cetiol ® V | Decyl Oleate | 4.0 |
| | Cetiol ® OE | Dicapryl Ether | 2.0 |
| | Baysilon ® M 350 | | 0.5 |
| | Glycerol 86% | | 3.0 |
| | Cationic biopolymer | | 5.0 |
| High Quality Skin Care Fluid | Emulgade ® PL 1618 | Hexadecyl Polyglucose (and) Hexadecyl Alcohol | 7.5 |
| | Cetiol ® J 600 | Oleyl Erucate | 4.0 |
| | Myritol ® 318 | Caprylic/Capric Triglyceride | 4.0 |
| | Cetiol ® V | Decyl Oleate | 4.0 |
| | Cetiol ® OE | Dicapryl Ether | 2.0 |
| | Baysilon ® M 350 | | 0.5 |
| | Glycerol 86% | | 3.0 |
| | Cationic biopolymer | | 10.0 |
| Skin Tonic | Ethanol (conc.) | | 15.0 |
| | Allantoin | | 0.3 |
| | Glycerol 86% | | 2.0 |

TABLE 2-continued

Skin Care Formulations*

| Example | Ingredient | CTFA Nomenclature | % Content |
|---|---|---|---|
| | Eumulgin ® HRE 40 | PEG 40 Hydrogenated Castor Oil | 1.0 |
| | Cationic biopolymer | | 2.5 |

*)All the quantities shown are percentages by weight. The formulations are made up to 100% by weight with water. The "cationic biopolymer" is the product of Production Example 1 in the form of a 1.5% by weight solution in glycolic acid.

What is claimed is:

1. A process for making a cationic biopolymer having an average molecular weight of 800,000 to 1,200,000 Dalton, a Brookfield viscosity (1% by weight in glycolic acid) of less than 5,000 mPas, a degree of deacetylation of 80 to 88% and an ash content of less than 0.3% by weight comprising the steps of: (a) contacting fresh crustacean shells with dilute aqueous mineral acid to form a first intermediate product; (b) contacting said first intermediate product with aqueous alkali metal hydroxide solution to form a second intermediate product; (c) contacting said second intermediate product with dilute aqueous mineral acid to produce a third intermediate product; (d) contacting said third intermediate product with a concentrated aqueous alkali metal hydroxide solution wherein steps (a) and (c) being carried out at a temperature of from about 15 to about 25° C. and at a pH of from about 0.3 to about 0.7 and steps (b) and (d) being carried out at a temperature of from about 70 to about 110° C. and at a pH of from about 12 to about 14.

2. The process of claim 1 wherein said third intermediate product is dried to a residual water content of from about 5 to about 25% by weight before step (d).

3. The process of claim 1 wherein said mineral acid is hydrochloric acid and said alkali metal hydroxide is sodium hydroxide.

4. A cationic biopolymer made by the process comprising the steps of: (a) contacting fresh crustacean shells with dilute aqueous mineral acid to form a first intermediate product; (b) contacting said first intermediate product with aqueous alkali metal hydroxide solution to form a second intermediate product; (c) contacting said second intermediate product with dilute aqueous mineral acid to produce a third intermediate product; (d) contacting said third intermediate product with a concentrated aqueous alkali metal hydroxide solution wherein steps (a) and (c) being carried out at a temperature of from about 15 to about 25° C. and at a pH of from about 0.3 to about 0.7 and steps (b) and (d) being carried out at a temperature of from about 70 to about 110° C. and at a pH of from about 12 to about 14.

5. The cationic biopolymer of claim 4 wherein said third intermediate product is dried to a residual water content of from about 5 to about 25% by weight before step (d).

6. The cationic biopolymer of claim 4 wherein said mineral acid is hydrochloric acid and said alkali metal hydroxide is sodium hydroxide.

7. A method of making a gelled hair or skin care product which comprises adding to a hair or skin care product from about 0.01% to about 5% by weight of a cationic biopolymer of claim 4.

8. The method of claim 7 wherein the weight of said cationic product is from about 0.10% to about 1.5% by weight.

* * * * *